(12) United States Patent
Wiltzius et al.

(10) Patent No.: US 11,572,388 B2
(45) Date of Patent: Feb. 7, 2023

(54) CHIMERIC POLYPEPTIDES AND USES THEREOF

(71) Applicant: Kite Pharma, Inc., Santa Monica, CA (US)

(72) Inventors: Jed J. W. Wiltzius, Winchester, MA (US); Stuart A. Sievers, Santa Monica, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 0 days.

(21) Appl. No.: 15/929,737

(22) Filed: May 19, 2020

(65) Prior Publication Data
US 2020/0399320 A1 Dec. 24, 2020

Related U.S. Application Data

(63) Continuation of application No. 16/138,331, filed on Sep. 21, 2018, now abandoned.

(60) Provisional application No. 62/562,223, filed on Sep. 22, 2017.

(51) Int. Cl.
| | | |
|---|---|---|
| *C07K 14/00* | (2006.01) | |
| *A61P 35/02* | (2006.01) | |
| *A61K 39/00* | (2006.01) | |
| *C07K 16/44* | (2006.01) | |
| *C07K 16/28* | (2006.01) | |
| *A61K 47/65* | (2017.01) | |
| *C07K 4/00* | (2006.01) | |
| *C07K 7/06* | (2006.01) | |
| *C07K 7/08* | (2006.01) | |
| *C12N 15/62* | (2006.01) | |
| *C12N 15/85* | (2006.01) | |

(52) U.S. Cl.
CPC ........ *C07K 14/003* (2013.01); *A61K 39/0011* (2013.01); *A61K 39/001112* (2018.08); *A61K 47/65* (2017.08); *A61P 35/02* (2018.01); *C07K 4/00* (2013.01); *C07K 7/06* (2013.01); *C07K 7/08* (2013.01); *C07K 16/2803* (2013.01); *C07K 16/44* (2013.01); *C12N 15/62* (2013.01); *C12N 15/85* (2013.01); *A61K 2039/5156* (2013.01); *A61K 2039/5158* (2013.01); *C07K 2317/32* (2013.01); *C07K 2317/34* (2013.01); *C07K 2317/622* (2013.01); *C07K 2319/40* (2013.01)

(58) Field of Classification Search
CPC .......... C07K 14/003; C07K 4/00; C07K 7/06; C07K 7/08; C07K 16/2803; C07K 16/44; C07K 2317/32; C07K 2317/34; C07K 2317/622; C07K 2319/40; C07K 14/001; A61K 39/0011; A61K 39/001112; A61K 47/65; A61K 2039/5156; A61K 2039/5158; A61P 35/02; C12N 15/62; C12N 15/85

See application file for complete search history.

(56) References Cited

U.S. PATENT DOCUMENTS

| | | | |
|---|---|---|---|
| 5,728,388 A | 3/1998 | Terman | |
| 6,541,610 B1 | 4/2003 | Smith | |
| 6,727,225 B2 | 4/2004 | Wiley | |
| 6,728,388 B1 | 4/2004 | Nageno et al. | |
| 7,056,683 B2 * | 6/2006 | Ting | C07K 14/47 435/194 |
| 10,501,775 B2 * | 12/2019 | Wiltzius | C07K 16/24 |
| 2002/0006409 A1 | 1/2002 | Wood | |
| 2006/0035387 A1 | 2/2006 | Wagner et al. | |
| 2006/0275868 A1 | 12/2006 | Smith | |
| 2007/0148739 A1 | 6/2007 | Jones et al. | |
| 2011/0020345 A1 | 1/2011 | Herring et al. | |
| 2013/0287748 A1 | 10/2013 | June et al. | |
| 2014/0050708 A1 | 2/2014 | Powell et al. | |
| 2014/0072581 A1 | 3/2014 | Dixit et al. | |
| 2014/0086907 A1 | 3/2014 | Shah | |
| 2014/0099309 A1 | 4/2014 | Powell, Jr. et al. | |
| 2014/0154228 A1 | 6/2014 | Volk et al. | |
| 2014/0227237 A1 | 8/2014 | June et al. | |
| 2014/0227264 A1 | 8/2014 | Hamilton et al. | |
| 2016/0017047 A1 * | 1/2016 | Poma | A61P 7/00 424/134.1 |
| 2016/0137711 A1 | 5/2016 | Schellenberger et al. | |
| 2016/0152723 A1 * | 6/2016 | Chen | C07K 16/2896 435/254.2 |
| 2016/0208018 A1 * | 7/2016 | Chen | A61P 43/00 |
| 2018/0280437 A1 * | 10/2018 | Wiltzius | A61K 35/17 |

FOREIGN PATENT DOCUMENTS

| | | |
|---|---|---|
| JP | 2014526254 A | 10/2014 |
| JP | 2015531751 A | 11/2015 |
| WO | 98036087 A1 | 8/1998 |
| WO | WO-02/059258 A2 | 8/2002 |

(Continued)

OTHER PUBLICATIONS

Lloyd et al., Protein Engineering, Design & Selection 22:159-168 (Year: 2009).*

(Continued)

*Primary Examiner* — Phuong Huynh

(57) ABSTRACT

The invention provides novel peptides (e.g., linkers) and polypeptide compositions comprising the linkers (e.g., fusion proteins) and methods of using the polypeptide compositions. Peptides (e.g., linkers) are useful as tags and for engineering fusion proteins (e.g., antigen binding molecules, scFv). Polypeptide linkers described herein facilitate flexibility of linked peptides allowing for proper folding, conformation and reduced immunogenicity.

7 Claims, 10 Drawing Sheets
Specification includes a Sequence Listing.

(56) References Cited

FOREIGN PATENT DOCUMENTS

| WO | 04044168 A2 | 5/2004 | |
|---|---|---|---|
| WO | 08081035 A1 | 7/2008 | |
| WO | 12106281 A2 | 8/2012 | |
| WO | 12138475 A1 | 10/2012 | |
| WO | WO-2016126950 A1 * | 8/2016 | .............. A61P 17/00 |
| WO | 17076916 A1 | 5/2017 | |

OTHER PUBLICATIONS

Edwards et al., J Mol Biol. 334(1): 103-118 (Year: 2003).*
Rudikoff et al., Proc Natl Acad Sci USA 79: 1979 (Year: 1982).*
Barrios et al., J Molecular Recognition 17: 332-338 (Year: 2004).*
MacCallum et al., J Mol. Biol 262: 732-745 (Year: 1996).*
Wu et al., J. Mol. Biol. 294: 151-162 (Year: 1999).*
Bird et al., "Single-Chain Antigen-Binding Proteins", Science 242:423-26 (1988).
Bruggemann et al., "Production of human antibody repertoires in transgenic mice", Curr. Opin. Biotechnol. 8:455-58 1997).
Cheung et al., "Epitope-specific antibody response to the surface antigen of duck hepatitis B virus in infected ducks", Virology, 176(2): 546-552 (1990).
Dayhoff et al., "Atlas of Protein Sequence and Structure: A Model of Evolutionary Change in Proteins", 5: 345-352 1978).
Devereux et al., "A comprehensive set of sequence analysis programs for the VAX", Nucl. Acid Res., 12: 387 (1984).
Henikoff et al., "Amino acid substitution matrices from protein blocks", Proc. Natl. Acad. Sci. U.S.A., 89(22): 10915-10919 (1992).
Huston et al., "Protein engineering of antibody binding sites: recovery of specific activity in an anti-digoxin single-chain Fv analogue produced in *Escherichia coli*", Proc Nat Acad Sci USA 85(16): 5879-5883 (1988).
Kirkland et al., "Analysis of the fine specificity and cross-reactivity of monoclonal anti-lipid A antibodies", J. Immunol. 37(11): 3614-3619 (1986).
Moldenhauer et al., "Identity of HML-1 antigen on intestinal intraepithelial T cells and of B-Iy7 antigen on hairy cell leukaemia", Scand. J. Immunol., 32(2): 77-82 (1990).
Morel et al., "Monoclonal antibodies to bovine serum albumin: affinity and specificity determinations", Molec. Immunol., 5(1): 7-15 (1988).
Nicholson et al., "Construction and characterisation of a functional CD19 specific single chain Fv fragment for immunotherapy of B lineage leukaemia and lymphoma", Mol Immunol., 34(16-17): 1157-65 (1997).
Stahli et al., "Distinction of epitopes by monoclonal antibodies", Methods in Enzymology, 92: 242-253 (1983).
Yusakul et al., "Effect of linker length between variable domains of single chain variable fragment antibody against daidzin on its reactivity", Biosci Biotechnol Biochem., 80(7): 1306-12 (2016).
NCBI Blast search of SEQ ID No. 5 downloaded Nov. 14, 2019 (Year: 2019).
NCBI Blast search of SEQ ID No. 6 downloaded Nov. 14, 2019 (Year: 2019).
NCBI Blast search of SEQ ID No. 7 downloaded Nov. 14, 2019 (Year: 2019).
NCBI Blast search of SEQ ID No. 8 downloaded Nov. 14, 2019 (Year: 2019).
NCBI Blast search of SEQ ID No. 9 downloaded Nov. 14, 2019 (Year: 2019).
NCBI Blast search of SEQ ID No. 10 downloaded Nov. 14, 2019 (Year: 2019).
NCBI Blast search of SEQ ID No. 11 downloaded Nov. 14, 2019 (Year: 2019).
NCBI Blast search of SEQ ID No. 12 downloaded Nov. 14, 2019 (Year: 2019).
NCBI Blast search of SEQ ID No. 17 downloaded Nov. 14, 2019 (Year: 2019).
NCBI Blast search of SEQ ID No. 18 downloaded Nov. 14, 2019 (Year: 2019).
NCBI Blast search of SEQ ID No. 19 downloaded Nov. 14, 2019 (Year: 2019).
NCBI Blast search of SEQ ID No. 20 downloaded Nov. 14, 2019 (Year: 2019).
Office Action, issued in JP Application No. 2020-516415, dated Mar. 16, 2021.
Examiner'S Requisition, issued in CA Application No. 3076099, dated Feb. 11, 2021.
Examination Report, issued in AU Application No. 2018338192, dated Mar. 24, 2021.
Communication Pursuant to Article 94(3), issued in EP Application No. 18788941.5, dated May 31, 2021.
Decision of Final Rejection dated Dec. 7, 2021 for Japanese Appl. No. 2020-516415.
Examination Report dated Dec. 2, 2021 for Australian Appl. No. 2018338192.
Inti. Search Report—Written Opinion dated Nov. 20, 2018 for PCT Intl. Appl. No. PCT/US2018/052184.
Office Action dated Jan. 21, 2022 for Canadian Appl. No. 3,076,099.
Office Action dated Mar. 14, 2022 for Korean Appl. No. 10-2020-7011148.
Office Action dated Nov. 21, 2022 for Canadian Appl. No. 3,076,099.

* cited by examiner

| | | |
|---|---|---|
| Whitlow Linker | GSTSGSGKPGSGEGSTKG | (SEQ ID NO: 1) |
| Whit Linker Trunc | STSGSGKPGSGEGST | (SEQ ID NO: 17) |
| G4S Linker | GGGGSGGGGSGGGGS | (SEQ ID NO: 2) |
| G4S2 Linker | GGGGSGGGGSGGGGSG | (SEQ ID NO: 18) |
| Kite Linker #1 | GGGGSGKPGSGGGGS | (SEQ ID NO: 9) |
| Kite Linker #2 | GGGGSGKPGSGEGGS | (SEQ ID NO: 10) |
| Kite Linker #3 | GGGGSGKPGSGEGGGS | (SEQ ID NO: 11) |
| Kite Linker #4 | GGGGSGKPGSGEGGGS | (SEQ ID NO: 7) |
| Kite Linker #5 | GGGGSGKPGSGEGGGGS | (SEQ ID NO: 12) |
| Kite Linker #6 | GGGGSGKPGSGEGGGGS | (SEQ ID NO: 8) |

Fig. 1

SEQUENCE LISTING

<160> NUMBER OF SEQ ID NOS: 33

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Thr Ser Gly Ser Gly Lys Pro Gly Ser Gly Glu Gly Ser Thr
1               5                   10                  15

Lys Gly

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Ser Gly Gly Gly Ser Gly Gly Gly Gly Ser
1               5                   10                  15

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Gly or Ser
<220> FEATURE:
<221> NAME/KEY: MOD_RES
<222> LOCATION: (11)..(13)
<223> OTHER INFORMATION: Gly or Ser
<220> FEATURE:
<221> NAME/KEY: MOD_RES
<222> LOCATION: (21)..(23)
<223> OTHER INFORMATION: Gly or Ser

<400> SEQUENCE: 3

Xaa Xaa Xaa Gly Lys Pro Gly Ser Gly Glu Xaa Xaa Xaa Gly Lys Pro
1               5                   10                  15

Gly Ser Gly Glu Xaa Xaa Xaa
            20

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Pro Gly Ser Gly Glu
1               5

<210> SEQ ID NO 5
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 5

Gly Lys Pro Gly Ser Gly Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Lys Pro Gly Ser Gly Gly
1               5

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Ser Gly Lys Pro Gly Ser Gly Glu Gly Gly Gly Ser
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Gly Ser Gly Lys Pro Gly Ser Gly Glu Gly Gly Gly Gly Ser
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser Gly Lys Pro Gly Ser Gly Gly Gly Gly Ser
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Ser Gly Lys Pro Gly Ser Gly Glu Gly Gly Ser
1               5                   10                  15
```

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Lys Pro Gly Ser Gly Glu Gly Gly Gly Ser
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Lys Pro Gly Ser Gly Glu Gly Gly Gly Gly
1               5                   10                  15

Ser

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Gly Lys Pro Gly Ser Gly Glu Gly
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Lys Pro Gly Ser Gly Glu Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gly Lys Pro Gly Ser Gly Glu
1               5

<210> SEQ ID NO 16
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 16

Lys Pro Gly Ser Gly
1               5

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Thr Ser Gly Ser Gly Lys Pro Gly Ser Gly Glu Gly Ser Thr
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser Gly Gly Gly Gly Ser Gly Gly Gly Gly Ser Gly
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Gly Ser Gly Gly Gly Gly Ser Gly Gly Gly Gly Ser
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ser Gly Gly Gly Gly Ser Gly Gly Gly Gly Gly Ser
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser Thr Ser Gly Ser Gly Lys Pro Gly Ser Gly Glu Gly Ser Thr
1               5                   10                  15

```
<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ser Thr Ser Gly Ser Gly Lys Pro Gly Ser Gly Glu Gly
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Ser Thr Ser Gly Ser Gly Lys Pro Gly Ser Gly Glu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ser Thr Ser Gly Ser Gly Lys Pro Gly Ser Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ser Thr Ser Gly Ser Gly Lys Pro Gly
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ser Gly Lys Pro Gly Ser Gly Glu Gly Ser Thr Lys Gly
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Ser Gly Lys Pro Gly Ser Gly Glu Gly Ser Thr Lys Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Lys Pro Gly Ser Gly Glu Gly Ser Thr Lys Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Pro Gly Ser Gly Glu Gly Ser Thr Lys Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Gly Ser Gly Glu Gly Ser Thr Lys Gly
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Gly Lys Pro Gly Ser Gly Glu Gly Gly
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Gly Gly Ser
1               5

<210> SEQ ID NO 33
<211> LENGTH: 7
<212> TYPE: PRT
<213> ORGANISM: Artificial Sequence
```

```
<220> FEATURE:
<223> OTHER INFORMATION: Consensus sequence
<220> FEATURE:
<221> NAME/KEY: MOD_RES
<222> LOCATION: (7)..(7)
<223> OTHER INFORMATION: X is Gly or a negatively charged amino acid

<400> SEQUENCE: 33

Gly Lys Pro Gly Ser Gly Xaa
1               5
```

CHIMERIC POLYPEPTIDES AND USES THEREOF

CROSS REFERENCE TO RELATED APPLICATIONS

This application is a continuation of U.S. patent application Ser. No. 16/138,331, filed Sep. 21, 2018, which claims priority to U.S. Provisional Application No. 62/562,223, filed Sep. 22, 2017, both of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Jun. 28, 2021, is named K1052PC2_ST25_2021 and is 8.8 kilobytes in size.

TECHNICAL FIELD

The present disclosure is directed to novel peptides and polypeptide compositions comprising such peptides (e.g., linkers, chimeric polypeptides, antigen biding molecules) and methods of using and preparing the same.

BACKGROUND

Antigen binding molecules, including antibodies, are used in immunotherapy and solid phase-based applications such as biosensors, affinity chromatography, and immunoassays. These antibodies and antigen binding molecules gain their utility by virtue of their ability to specifically bind their targets.

Fusion proteins may require linker sequences, which are often peptide-based when employed in biotechnological and biotherapeutic applications, which may serve a range of scientifically-relevant applications. For example, a linker may be used as a spacer moiety in order to impart a desired structural and/or functional property to a larger molecule. In another example, a linker may impart little or no structural or functional properties to a larger molecule, but may be used simply as a distinguishing feature (e.g., a "marker" or "biomarker" or "tag"), uniquely identifying a larger molecule. In still another example, a linker may be used to impart a recognizable feature that may serve as a binding site for an antibody directed against a larger molecule comprising the peptide sequence.

SUMMARY

The present invention provides, among other things, novel peptide sequences which allow for the proper expression, folding, identification and activity of a fusion protein. The novel peptides described herein, may be used for connecting domains within a fusion protein (e.g., scFvs) facilitating flexibility of the individual peptide domains. ScFv s comprise the binding domain of most CAR constructs. A scFv comprises IgG variable light and heavy chains and a flexible peptides (e.g., linker) connecting these two domains. A linker must be long enough to connect the domains into a single protein construct. Further, it is desirable that a linker or tag construct not be a potential cause of immunogenicity.

Commonly used linkers include repeats of glycine-glycine-glycine-glycine-serine (G4S) (SEQ ID NO: 32) due to their intrinsic flexibility and simplicity of side chains, which may be less immunogenic in therapeutic applications. The 18-residue Whitlow linker GSTSGSGKPGSGEGSTKG (SEQ ID NO: 1), was first described by Whitlow et al. in 1993. The peptides described herein, may also be used as a peptide tag. In some embodiments, the fusion protein comprises a polypeptide fused to a peptide (e.g., a linker) described herein.

Novel chimeric polypeptides described herein comprising a consensus sequence BPXXXZ combine desirable attributes (e.g., flexibility and reduced immunogenicity) suitable for incorporation into fusion proteins useful for therapeutic intervention.

In one aspect, the present invention provides a peptide comprising 6-20 amino acids and a consensus sequence BPXXXZ, wherein X is a glycine (G) or serine (S), B is a positively charged amino acid and Z is glycine (G) or a negatively charged amino acid. In one embodiment, the present invention provides a peptide, wherein the consensus sequence is KPGSGE (SEQ ID NO: 4). In another embodiment, the consensus sequence is GKPGSGE (SEQ ID NO: 5) or GKPGSGG (SEQ ID NO: 6).

In one aspect, the present invention provides a peptide comprising 6-20 amino acids and a consensus sequence BPXXXZ, wherein X is a glycine (G) or serine (S), B is a positively charged amino acid and Z is glycine (G) or a negatively charged amino acid, and wherein the peptide is not GSTSGSGKPGSGEGSTKG (SEQ ID NO: 1), GSGKPGSGEG (SEQ ID NO: 13), GKPGSGEG (SEQ ID NO: 14), or SGKPGSGE (SEQ ID NO: 15).

In one aspect, the present invention provides a peptide comprising 8-20 amino acids and a consensus sequence XBPXXXZX, wherein each X is independently a glycine (G) or serine (S), B is a positively charged amino acid and Z is glycine (G) or a negatively charged amino acid and P is proline.

In one aspect, the present invention provides a peptide comprising 8-20 amino acids and a consensus sequence XBPXXXZX, wherein each X is independently a glycine (G) or serine (S), B is a positively charged amino acid and Z is glycine (G) or a negatively charged amino acid and P is proline, and wherein the peptide is not GSTSGSGKPGSGEGSTKG (SEQ ID NO: 1), GSGKPGSGEG (SEQ ID NO: 13), GKPGSGEG (SEQ ID NO: 14), or SGKPGSGE (SEQ ID NO: 15).

In some embodiments, the present invention provides a peptide comprising 8-20 amino acids and a consensus sequence XBPXXXZX, wherein each X is independently a glycine (G) or serine (S), B is lysine (K) or arginine (R), and Z is glycine (G) or a negatively charged amino acid, and P is proline.

In some embodiments, the present invention provides a peptide comprising 8-20 amino acids and a consensus sequence XBPXXXZX, wherein X is independently a glycine (G) or serine (S), B is lysine (K), and Z is glycine (G) or a negatively charged amino acid, and P is proline.

In some embodiments, the present invention provides a peptide comprising 8-20 amino acids and a consensus sequence XBPXXXZX, wherein each X is independently a glycine (G) or serine (S), B is a positively charged amino acid, and Z is glycine (G) and P is proline.

In some embodiments, Z is a negatively charged amino acid selected from glutamic acid (E) or aspartic acid (D). In some embodiments, Z is glutamic acid (E).

In some embodiments, the present invention provides a peptide, wherein the consensus sequence is GKPGSGE (SEQ ID NO: 5) or GKPGSGG (SEQ ID NO: 6). In some embodiments, the consensus sequence is GKPGSGE (SEQ ID NO: 5). In some embodiments, the peptide comprises the consensus sequence GSGKPGSGEGG (SEQ ID NO: 31).

In some embodiments, the peptide comprises one or more repeats of the consensus sequence. In some embodiments, the repeats are contiguous. In some embodiments, the peptide repeats are separated by 1-4 amino acids. In some embodiments, the peptide is xxxGKPGSGExxxGKPGSGExxx (SEQ ID NO: 3), wherein X is a glycine (G) or serine (S).

In some embodiments, the peptide is not GST-SGSGKPGSGEGSTKG (SEQ ID NO: 1), GSGKPGSGEG (SEQ ID NO: 13), GKPGSGEG (SEQ ID NO: 14), or SGKPGSGE (SEQ ID NO: 15). In certain embodiments, the peptide is not GSTSGSGKPGSGEGSTKG (SEQ ID NO: 1). In certain embodiments, the linker is not GSGKPGSGEG (SEQ ID NO: 13). In certain embodiments, the peptide is not GKPGSGEG (SEQ ID NO: 14). In certain embodiments, the peptide is not SGKPGSGE (SEQ ID NO: 15).

In some embodiments, the peptide comprises 6-20 amino acids. In some embodiments, the peptide comprises 10-20 amino acids. In some embodiments, the peptide comprises 14-19 amino acids. In some embodiments, the peptide comprises 15-17 amino acids. In some embodiments, the peptide comprises 15-16 amino acids. In some embodiments, the peptide comprises 16 amino acids.

In some embodiments, the peptide comprises an amino acid sequence of GGGSGKPGSGEGGGS (SEQ ID NO: 7). In some embodiments, the peptide comprises an amino acid sequence of GGGSGKPGSGEGGGGS (SEQ ID NO: 8). In some embodiments, the peptide comprises an amino acid sequence of GGGGSGKPGSGGGGS (SEQ ID NO: 9). In some embodiments, the peptide comprises an amino acid sequence of GGGGSGKPGSGEGGS (SEQ ID NO: 10). In some embodiments, the peptide comprises an amino acid sequence of GGGGSGKPGSGEGGGS (SEQ ID NO: 11). In some embodiments, the peptide comprises an amino acid sequence of GGGGSGKPGSGEGGGGS (SEQ ID NO: 12). In some embodiments, the peptide comprises an amino acid sequence of STSGSGKPGSGEGST (SEQ ID NO: 17). In some embodiments, the peptide comprises an amino acid sequence of GGGGSGGGGSGGGGSG (SEQ ID NO: 18). In some embodiments, the peptide comprises an amino acid sequence of GGGGGSGGGGSGGGGS (SEQ ID NO: 19). In some embodiments, the peptide comprises an amino acid sequence of GGGGSGGGGSGGGGS (SEQ ID NO: 20).

In one aspect, the present invention provides a peptide comprising 8-20 amino acids and an amino acid sequence at least 80% identical to any one of GGGSGKPGSGEGGGS (SEQ ID NO: 7), GGGSGKPGSGEGGGGS (SEQ ID NO: 8), GGGGSGKPGSGGGGS (SEQ ID NO: 9), GGGGSGKPGSGEGGS (SEQ ID NO: 10), GGGGSGKPGSGEGGGS (SEQ ID NO: 11), GGGGSGKPGSGEGGGGS (SEQ ID NO: 12), STSGSGKPGSGEGST (SEQ ID NO: 17), GGGGSGGGGSGGGGSG (SEQ ID NO: 18), GGGGGSGGGGSGGGGS (SEQ ID NO: 19), or GGGGSGGGGSGGGGS (SEQ ID NO: 20).

In some embodiments, the peptide comprises an amino acid sequence that is at least 90% identical to any one of GGGSGKPGSGEGGGS (SEQ ID NO:7), GGGSGKPGSGEGGGGS (SEQ ID NO:8), GGGGSGKPGSGGGGS (SEQ ID NO:9), GGGGSGKPGSGEGGS (SEQ ID NO: 10), GGGGSGKPGSGEGGGS (SEQ ID NO: 11), GGGGSGKPGSGEGGGGS (SEQ ID NO: 12), STSGSGKPGSGEGST (SEQ ID NO: 17), GGGGSGGGGSGGGGSG (SEQ ID NO: 18), GGGGGSGGGGSGGGGS (SEQ ID NO: 19), or GGGGSGGGGSGGGGS (SEQ ID NO: 20).

In one aspect, the present invention provides a peptide comprising 8-20 amino acids and an amino acid sequence that contains at least six (6) identical amino acids out of ten (10) contiguous amino acids found in any one of GGGSGKPGSGEGGGS (SEQ ID NO: 7), GGGSGKPGSGEGGGGS (SEQ ID NO: 8), GGGGSGKPGSGGGGS (SEQ ID NO: 9), GGGGSGKPGSGEGGS (SEQ ID NO: 10), GGGGSGKPGSGEGGGS (SEQ ID NO: 11), GGGGSGKPGSGEGGGGS (SEQ ID NO: 12), STSGSGKPGSGEGST (SEQ ID NO: 17), GGGGSGGGGSGGGGSG (SEQ ID NO: 18), GGGGGSGGGGSGGGGS (SEQ ID NO: 19), or GGGGSGGGGSGGGGS (SEQ ID NO: 20).

In some embodiments, the peptide amino acid sequence contains at least seven (7), at least eight (8) or at least nine (9) identical amino acids out of ten (10) contiguous amino acids found in any one of GGGSGKPGSGEGGGS (SEQ ID NO: 7), GGGSGKPGSGEGGGGS (SEQ ID NO: 8), GGGGSGKPGSGGGGS (SEQ ID NO: 9), GGGGSGKPGSGEGGS (SEQ ID NO: 10), GGGGSGKPGSGEGGGS (SEQ ID NO: 11), GGGGSGKPGSGEGGGGS (SEQ ID NO: 12), STSGSGKPGSGEGST (SEQ ID NO: 17), GGGGSGGGGSGGGGSG (SEQ ID NO: 18), GGGGGSGGGGSGGGGS (SEQ ID NO: 19), or GGGGSGGGGSGGGGS (SEQ ID NO: 20).

In some embodiments, the peptide comprises an amino acid sequence of GGGGSGGGGSGGGGSG (SEQ ID NO: 18), GGGGGSGGGGSGGGGS (SEQ ID NO: 19), or GGGGSGGGGSGGGGS (SEQ ID NO: 20).

In one aspect, the present invention provides a fusion protein comprising a first polypeptide; a second polypeptide; and a peptide linker as described herein. In some aspects, the fusion protein is an antigen binding molecule. In some embodiments, the antigen binding molecule is a scFv. In some embodiments, the first polypeptide is a light chain variable domain and the second polypeptide is a heavy chain variable domain. In some embodiments, the fusion protein is a chimeric antigen receptor.

In one aspect, the present invention provides a polynucleotide encoding a peptide (e.g., linker, tag) as described herein. In some embodiments, the present invention provides a polynucleotide encoding a fusion protein as described herein.

In one aspect, the present invention provides an expression vector comprising a polynucleotide encoding a peptide (e.g., a linker or fusion protein) as described herein. In some embodiments, the present invention provides a recombinant cell comprising a polynucleotide encoding a peptide (e.g., a linker or fusion protein) as described herein. In some embodiments, the recombinant cell comprises an expression vector comprising a polynucleotide encoding a peptide (e.g., a linker or fusion protein) as described herein.

Any aspect or embodiment described herein may be combined with any other aspect or embodiment as disclosed herein. While the present invention has been described in conjunction with the detailed description thereof, the foregoing description is intended to illustrate and not limit the scope of the present invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, dictionaries, documents, manuscripts and scientific literature cited herein are hereby incorporated by reference.

Other features and advantages of the invention will be apparent from the Drawings and the following Detailed Description, including the Examples, and the claims.

BRIEF DESCRIPTION OF THE DRAWING

The above and further features will be more clearly appreciated from the following detailed description when taken in conjunction with the accompanying drawings. The drawings however, are for illustration purposes only, not for limitation.

FIG. 1 shows an amino acid sequence alignment of exemplary peptide (e.g., linker) sequences.

DEFINITIONS

Figure 2:
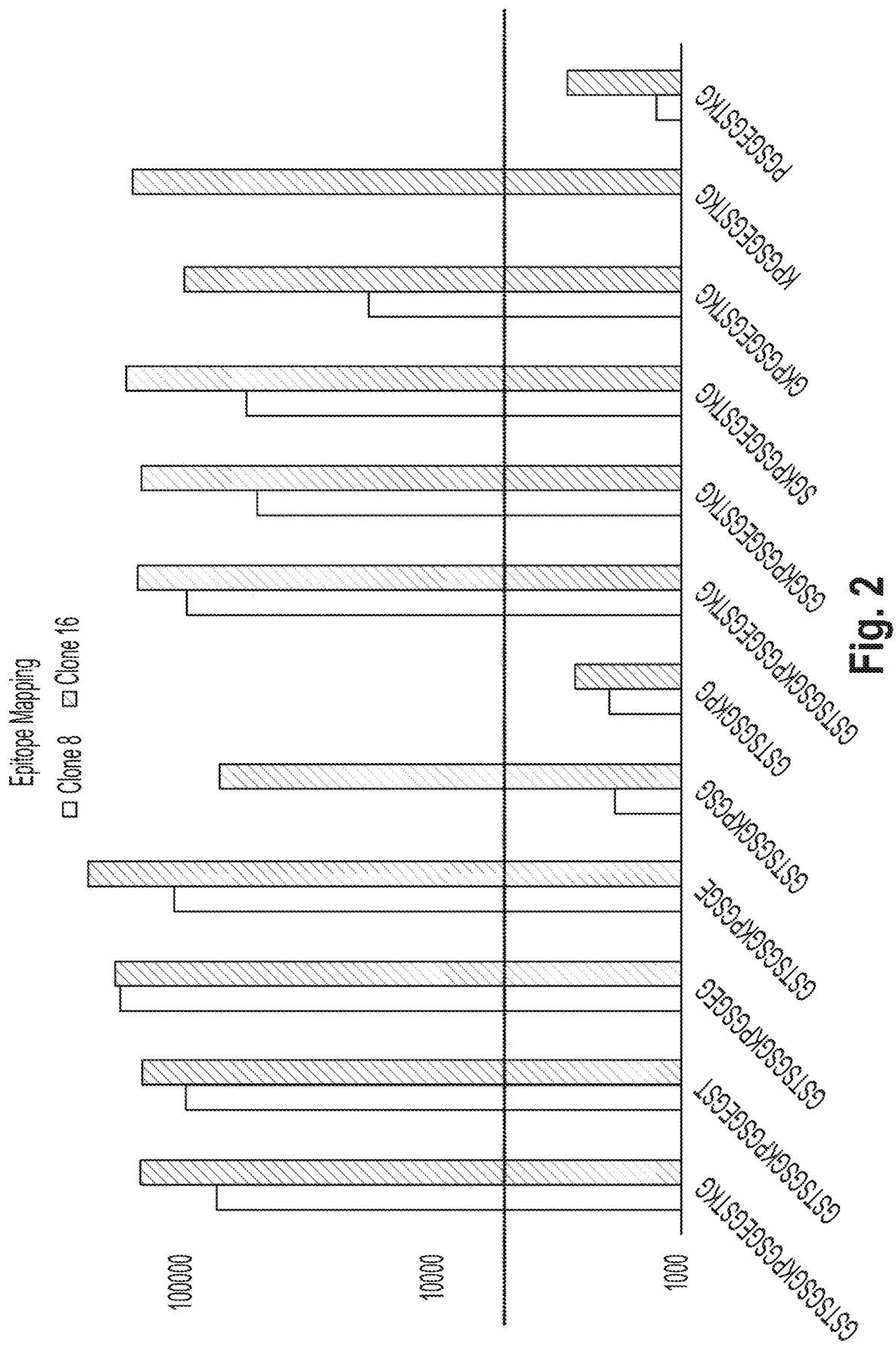
FIG. 2 shows a bar graph of results of an epitope mapping ELISA experiment of peptides comprising SEQ ID NOs 1, 21-25, 1 and 26-30, respectively.

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and."

The term "and/or" where used herein is to be taken as specific disclosure of each of the two specified features or components with or without the other. Thus, the term "and/or" as used in a phrase such as "A and/or B" herein is intended to include A and B, A or B, A (alone), and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" may mean within one or more than one standard deviation per the practice in the art. "About" or "comprising essentially of" may mean a range of up to 10% (i.e., ±10%). Thus, "about" may be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Systeme International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intra-arterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal, or mucosal route of administration, for example, intranasally, vaginally, rectally, sublingually or topically. Administering may also be performed, for example, once, a plurality of times, and/or over one or more extended periods.

As used herein, an antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition may be complete, e.g., binding of the binding molecule to the antigen completely blocks the ability of the reference binding molecule to bind the antigen, or it may be partial, e.g., binding of the binding molecule to the antigen reduces the ability of the reference binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays may be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15), solid phase direct biotin-avidin EIA (Cheung, et al., 1990, Virology 176:546-552), and direct labeled RIA (Moldenhauer et al., 1990, Scand. J. Immunol. 32:77-82).

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, could serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In one embodiment, antigens are tumor antigens.

The term "allogeneic" refers to any material derived from one individual, which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may metastasize to distant parts of the body through the lymphatic system or bloodstream. A "cancer" or "cancer tissue" may include a tumor. Examples of cancers that may be treated by the methods of the present invention include, but are not limited to, cancers of the immune system including lymphoma, leukemia, myeloma, and other leukocyte malignancies. In some embodiments, the methods of the present invention may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer may be responsive to chemo- or radiation therapy or the cancer may be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. A cytokine may be endogenously expressed by a cell or administered to a subject. Cytokines may be released by immune cells, including macrophages, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p'70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression may be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory TSCM cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). They make antibodies and antigens, perform the role of antigen-presenting cells (APCs), and turn into memory B-cells after activation by antigen interaction. In mammals, immature B-cells are formed in the bone marrow.

The term "genetically engineered", "engineered", or "modified" refers to a method of modifying a cell, including, but not limited to, creating a deficiency in a gene by deleting a coding or non-coding region or a portion thereof or by antisense technology, or increasing expression of a protein introducing a coding region or a portion thereof. In some embodiments, the cell that is modified is a stem cell (e.g., hematopoietic stem cell (HSC), embryonic stem cell (ES), induced pluripotent stem (iPS) cell), lymphocyte (e.g., a T cell), which may be obtained either from a patient or a donor. The cell may be modified to express an exogenous construct, such as, e.g., a pre-TCR alpha protein, a chimeric antigen receptor (CAR) or a T cell receptor (TCR), which may be incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing, or otherwise modifying an immune response. Examples of immunotherapy include, but are not limited to, T cell therapies. T cell therapy may include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy may come from any source known in the art. For example, T cells may be differentiated in vitro from a hematopoietic stem cell population; induced pluripotent stem cells (iPS), embryonic stem cells (ES), or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which may be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell may include a T cell.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that may comprise a protein or peptide's sequence. As used herein, peptides of the present invention may function as a linker (e.g., joining two peptides or polypeptides). As used herein, peptides of the present invention may function as a biomarker or tag. The terms peptide, tag, or linker are used interchangeably. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, which specifically binds with a cognate stimulatory ligand present on an antigen present cell. A "stimulatory ligand" is a ligand that when present on an antigen presenting cell (e.g., an APC, a dendritic cell, a B-cell, and the like) may specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand" as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta;

delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-la, CD1-lb, CD1-lc, CD1-ld, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD1 la/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein, and indicate any change that is less than the original. "Reducing" and "decreasing" are relative terms, requiring a comparison between pre- and post-measurements "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity, or recurrence of a symptom, complication or condition, or biochemical indicia associated with a disease. In one embodiment, "treatment" or "treating" includes a partial remission. In another embodiment, "treatment" or "treating" includes a complete remission.

To calculate percent identity, the sequences being compared are typically aligned in a way that gives the largest match between the sequences. One example of a computer program that may be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm.) In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Various aspects of the invention are described in further detail in the following subsections.

DETAILED DESCRIPTION

Compositions are described herein that provide a means to make (e.g., design, engineer) chimeric or fusion polypeptides. A peptide (e.g., linker) sequence as described herein allows for the proper expression, folding and activity of a fusion protein. The present invention provides, among other things, novel polypeptides (e.g., linkers) and fusion proteins comprising the same. In some embodiments, the present invention provides polynucleotide compositions encoding a peptide (e.g., linker, tag) or fusion protein described herein. In some embodiments, the present invention provides an expression vector comprising the polynucleotide encoding a peptide (e.g., linker, tag) or fusion protein. In other embodiments, the present invention provides a cell comprising the polynucleotide and/or the expression vector encoding a peptide (e.g., linker, tag) or fusion protein. Described herein are novel compositions comprising peptide linkers, polypeptide compositions comprising polypeptides joined by the peptide linkers and related polynucleotides, vectors, cells and pharmaceutical compositions. In some embodiments, the peptide (e.g., linker, tag) is fused to one or more polypeptides. Described linker sequences operably join two peptides/polypeptides of interest such that the expression and activity (e.g., antigen binding) of the polypeptides connected by the linkers are durable and optimal. The peptide linker or tag may be fused at the C-terminus, N-terminus, or anywhere within the polypeptide to achieve the desired function.

Peptide Linkers

Novel chimeric polypeptide linkers described herein comprising a consensus sequence XYPXXXZX combine desirable attributes suitable for incorporation into fusion proteins useful for therapeutic intervention. In one aspect, the present invention provides a linker comprising 8-20 amino acids and a consensus sequence XYPXXXZX, wherein X is a glycine (G) or serine (S), B is a positively charged amino acid and Z is glycine (G) or a negatively charged amino acid. The inventors have discovered that both the spacing and charge of the of the amino acid residues in the consensus sequence contribute to functionality of the linker in addition to antibody recognition of the linker sequence.

In one aspect, the present invention provides a linker comprising 6-20 amino acids and a consensus sequence BPXXXZ, wherein X is a glycine (G) or serine (S), B is lysine (K) or arginine (R), and Z is glycine (G) or a negatively charged amino acid, and P is proline.

In some embodiments, the present invention provides a linker comprising 8-20 amino acids and a consensus sequence XBPXXXZX, wherein X is a glycine (G) or serine (S), B is lysine (K) or arginine (R), and Z is glycine (G) or a negatively charged amino acid, and P is proline.

In some embodiments, the present invention provides a linker comprising 8-20 amino acids and a consensus sequence XBPXXXZX, wherein X is a glycine (G) or serine (S), B is lysine (K), and Z is glycine (G) or a negatively charged amino acid, and P is proline.

In some embodiments, the present invention provides a linker comprising 8-20 amino acids and a consensus sequence XBPXXXZX, wherein X is a Glycine (G) or serine (S), B is a positively charged amino acid, and Z is glycine (G), and P is proline.

In some embodiments, Z is a negatively charged amino acid selected from glutamic acid (E) or aspartic acid (D). In some embodiments, Z is glutamic acid (E).

In some embodiments, the present invention provides a linker, wherein the consensus sequence is GKPGSGE (SEQ ID NO: 5) or GKPGSGG (SEQ ID NO: 6). In some embodiments, the consensus sequence is GKPGSGE (SEQ ID NO: 5).

In some embodiments, the peptide comprises an amino acid sequence of GGGGSGGGGSGGGGSG (SEQ ID NO: 18).

The linker peptide sequence may be of any appropriate length to connect one or more proteins of interest and is preferably designed to be sufficiently flexible so as to allow the proper folding and/or function and/or activity of one or both of the peptides it connects. Thus, the linker peptide may have a length of no more than 10, no more than 11, no more than 12, no more than 13, no more than 14, no more than 15, no more than 16, no more than 17, no more than 18, no more than 19, or no more than 20 amino acids. In some embodiments, the linker peptide may have a length of at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids. In some embodiments, the linker comprises at least 7 and no more than 20 amino acids, at least 7 and no more than 19 amino acids, at least 7 and no more than 18 amino acids, at least 7 and no more than 17 amino acids, at least 7 and no more than 16 amino acids, at least 7 and no more 15 amino acids, at least 7 and no more than 14 amino acids, at least 7 and no more than 13 amino acids, at least 7 and no more than 12 amino acids or at least 7 and no more than 11 amino acids. In certain embodiments, the linker comprises 15-17 amino acids, and in particular embodiments, comprises 16 amino acids. In some embodiments, the linker comprises 10-20 amino acids. In some embodiments, the linker comprises 14-19 amino acids. In some embodiments, the linker comprises 15-17 amino acids. In some embodiments, the linker comprises 15-16 amino acids. In some embodiments, the linker comprises 16 amino acids. In some embodiments, the linker comprises 10, 11, 12, 13, 14, 15, 16, 17, 18, 19 or 20 amino acids.

As used herein, a "conservative amino acid substitution" is one in which the amino acid residue is replaced with an amino acid residue having a similar side chain. Families of amino acid residues having side chains have been defined in the art. These families include amino acids with basic or positively charged side chains (e.g., lysine, arginine, histidine), acidic or negatively charged side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a polypeptide linker, fusion protein, CDR(s) or within a framework region(s) of an antibody or antigen binding molecule provided herein (or fragment thereof) may be replaced with an amino acid residue with a similar side chain.

Conservative amino acid substitutions, which are encompassed by the present disclosure, may encompass non-naturally occurring amino acid residues, which are typically incorporated by chemical peptide synthesis rather than by synthesis in biological systems. These include peptidomimetics and other reversed or inverted forms of amino acid moieties. Naturally occurring residues may be divided into classes based on common side chain properties:
  hydrophobic: norleucine, Met, Ala, Val, Leu, Ile;
    neutral hydrophilic: Cys, Ser, Thr, Asn, Gln;
      acidic (negatively charged): Asp, Glu;
      basic (negatively charged): His, Lys, Arg;
  residues that influence chain orientation: Gly, Pro; and
    aromatic: Trp, Tyr, Phe.

Non-conservative substitutions may involve the exchange of a member of one of these classes for a member from another class. Such substituted residues may be introduced, for example, into regions of a human antibody that are homologous with non-human antibodies, or into the non-homologous regions of the molecule. Exemplary conservative amino acid substitutions are set forth in Table A below.

TABLE A

| Original Residues | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4 Diamino-butyric acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

In some embodiments, the linker comprises an amino acid sequence of GGGSGKPGSGEGGGS (SEQ ID NO: 7). In some embodiments, the linker comprises an amino acid sequence of GGGSGKPGSGEGGGGS (SEQ ID NO: 8). In some embodiments, the linker comprises an amino acid sequence of GGGGSGKPGSGGGGS (SEQ ID NO: 9). In some embodiments, the linker comprises an amino acid sequence of GGGGSGKPGSGEGGS (SEQ ID NO: 10). In some embodiments, the linker comprises an amino acid sequence of GGGGSGKPGSGEGGGS (SEQ ID NO: 11). In some embodiments, the linker comprises an amino acid sequence of GGGGSGKPGSGEGGGGS (SEQ ID NO: 12). In some embodiments, the linker comprises an amino acid sequence of STSGSGKPGSGEGST (SEQ ID NO: 17). In some embodiments, the peptide comprises an amino acid sequence of GGGGSGGGGSGGGGSG (SEQ ID NO: 18). In some embodiments, the peptide comprises an amino acid sequence of GGGGGSGGGGSGGGGS (SEQ ID NO: 19). In some embodiments, the peptide comprises an amino acid sequence of GGGGSGGGGSGGGGGS (SEQ ID NO: 20).

In one aspect, the present invention provides a linker comprising 6-20 amino acids and an amino acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to any one of GGGSGKPGSGEGGGS (SEQ ID NO: 7), GGGSGKPGSGEGGGGS (SEQ ID NO:8), GGGGSGKPGSGGGGS (SEQ ID NO: 9), GGGGSGKPGSGEGGS (SEQ ID NO: 10), GGGGSGKPGSGEGGGS (SEQ ID NO: 11), GGGGSGKPGSGEGGGGS (SEQ ID NO: 12), STSGSGKPGSGEGST (SEQ ID NO: 17), GGGGSGGGGSGGGGSG (SEQ ID NO: 18), GGGGGSGGGGSGGGGS (SEQ ID NO: 19) or GGGGSGGGGSGGGGGS (SEQ ID NO: 20).

In some embodiments, the linker amino acid sequence contains at least five (5), six (6), seven (7), eight (8) or at least nine (9) identical amino acids out of ten (10) contiguous amino acids found in any one of GGGSGKPGSGEGGGS (SEQ ID NO: 7), GGGSGKPGSGEGGGGS (SEQ ID NO: 8), GGGGSGKPGSGGGGS (SEQ ID NO: 9), GGGGSGKPGSGEGGS (SEQ ID NO: 10), GGGGSGKPGSGEGGGS (SEQ ID NO: 11), GGGGSGKPGSGEGGGGS (SEQ ID NO: 12), STSGSGKPGSGEGST (SEQ ID NO: 17), GGGGSGGGGSGGGGSG (SEQ ID NO: 18), or GGGGGSGGGGSGGGGS (SEQ ID NO: 19) or GGGGSGGGGSGGGGGS (SEQ ID NO: 20).

In one aspect, the present invention provides a linker comprising 8-20 amino acids and an amino acid sequence that contains at least six (6) identical amino acids out of ten (10) contiguous amino acids found in any one of GGGSGKPGSGEGGGS (SEQ ID NO: 7), GGGSGKPGSGEGGGGS (SEQ ID NO: 8), GGGGSGKPGSGGGGS (SEQ ID NO: 9), GGGGSGKPGSGEGGS (SEQ ID NO: 10), GGGGSGKPGSGEGGGS (SEQ ID NO: 11), GGGGSGKPGSGEGGGGS (SEQ ID NO: 12), STSGSGKPGSGEGST (SEQ ID NO: 17), GGGGSGGGGSGGGGSG (SEQ ID NO: 18), GGGGGSGGGGSGGGGS (SEQ ID NO: 19) or GGGGSGGGGSGGGGGS (SEQ ID NO: 20).

In some embodiments, the linker amino acid sequence contains at least seven (7), at least eight (8) or at least nine (9) identical amino acids out of ten (10) contiguous amino acids found in any one of GGGSGKPGSGEGGGS (SEQ ID NO: 7), GGGSGKPGSGEGGGGS (SEQ ID NO: 8), GGGGSGKPGSGGGGS (SEQ ID NO: 9), GGGGSGKPGSGEGGS (SEQ ID NO: 10), GGGGSGKPGSGEGGGS (SEQ ID NO: 11), or GGGGSGKPGSGEGGGGS (SEQ ID NO: 12), STSGSGKPGSGEGST (SEQ ID NO: 17), GGGGSGGGGSGGGGSG (SEQ ID NO: 18), GGGGGSGGGGSGGGGS (SEQ ID NO: 19) or GGGGSGGGGSGGGGGS (SEQ ID NO: 20).

Fusion Protein

In one aspect, the present invention provides a fusion protein comprising a first polypeptide; a second polypeptide; and a linker as described herein. Polypeptide composition and polynucleotides encoding the polypeptide compositions are described herein, in which the polypeptide compositions comprise a first and second peptide/polypeptide, connected by a linker sequence disclosed herein. The inventors have surprisingly found that a linker according to the present invention provides both optimal flexibility of the first and second peptide and length to avoid steric hindrance and allow correct folding.

Polypeptide compositions produced in this manner are commonly referred to a fusion or chimeric protein/polypeptides and typically are made by the expression (e.g., transcription, translation) of nucleic acid sequences encoding the polypeptide compositions, in the appropriate system. Means by which to make fusion and/or chimeric polypeptides are well-known in the art (see for example, Sambrook et al., Molecular Cloning: A Laboratory Manual, Cold Springs Harbor Laboratory, 1992) New York which is incorporated by reference herein in its entirety).

In the polypeptide compositions described herein, the two polypeptides (e.g., a first polypeptide and a second polypeptide) may be recombinantly joined by any of the linker polypeptides described above, with the linker disposed between the two polypeptides. For example, in certain embodiments, the polypeptides or compositions comprise a first and a second polypeptide recombinantly joined by a linker comprising GGGSGKPGSGEGGGS (SEQ ID NO: 7), GGGSGKPGSGEGGGGS (SEQ ID NO: 8), GGGGSGKPGSGGGGS (SEQ ID NO: 9), GGGGSGKPGSGEGGS (SEQ ID NO: 10), GGGGSGKPGSGEGGGS (SEQ ID NO: 11), GGGGSGKPGSGEGGGGS (SEQ ID NO: 12), STSGSGKPGSGEGST (SEQ ID NO: 17), GGGGSGGGGSGGGGSG (SEQ ID NO: 18), GGGGGSGGGGSGGGGS (SEQ ID NO: 19) or GGGGSGGGGSGGGGGS (SEQ ID NO: 20). The two polypeptides may be any amino acid sequences including full-length proteins, protein fragments or portions, functional protein fragments or portions, functional protein domains and the like, of either two different proteins or the same protein.

As used herein, the term "polypeptide" or "peptide" refers a polymer of amino acid residues typically joined exclusively by peptide bonds, that may be produced naturally (e.g., isolated, essentially purified or purified) or synthetically (e.g., by chemical synthesis). A polypeptide produced by expression of a non-host DNA molecule is a "heterologous" peptide or polypeptide. An "amino acid residue" comprising the polypeptide may be a natural or non-natural amino acid residue linked by peptide bonds and/or bonds different from peptide bonds. The amino acid residues may be in D-configuration or L-configuration. In some aspects, the polypeptides referred to herein are proteins, peptides or fragments thereof produced by the expression of recombinant nucleic acid. In some embodiments, the polypeptide compositions described herein comprise two polypeptides connected by a linker sequence.

As used herein, "functional fragment" or "portion" is intended to refer to less than the entire mature or native protein which is sufficient to retain one or more of the desired biological activities of the mature or native protein (e.g., sufficient to retain a therapeutic or ameliorative biological activity with respect to a disorder to be treated). Thus, amino acid sequences or polypeptides may be modified, for example, polypeptide sequences into which amino acids have been inserted, deleted and/or substituted in such a manner that the modifications do not substantially interfere with the polypeptide's ability to encode a functional agent.

The linker or polypeptide linker described herein refers to a peptide sequence designed to connect (e.g., join, link) two protein sequences, wherein the linker peptide sequence is typically not disposed between the two protein sequences in nature. In the context of the present invention, the phrase "linked" or "joined" or "connected" generally refers to a functional linkage between two contiguous or adjacent amino acid sequences to produce a polypeptide that generally does not exist in nature. In certain embodiments, linkage may be used to refer to a covalent linkage of, for example, the amino acid sequences of a first polypeptide and the second polypeptide (e.g., antibody heavy chain and light chain). Generally, linked proteins are contiguous or adjacent to one another and retain their respective operability and function when joined. Peptides comprising the chimeric polypeptides disclosed herein are linked by means of an interposed peptide linker comprising one or more amino acids. Such linkers may provide desirable flexibility to permit the desired expression, activity and/or conformational positioning of the chimeric polypeptide. A typical amino acid linker is generally designed to be flexible or to interpose a structure, such as an alpha-helix, between the two protein moieties. A linker may be fused to the N-terminus or C-terminus of a polypeptide, or inserted internally.

In a polypeptide composition comprising a linker, the 5' end (e.g., terminus) of the linker peptide sequence (e.g., amino acid sequence) is adjacent to and covalently linked to the 3' end of one protein sequence (first peptide) (e.g., full-length protein or protein domain, fragment or variant)

and, further, the 3' end of the linker amino acid sequence is adjacent to and covalently linked to the 5' end of another protein sequence (second peptide).

Antigen Binding Molecules

In some aspects, the fusion protein is an antigen binding molecule. In some embodiments, the first polypeptide is a light chain variable domain and the second polypeptide is a heavy chain variable domain. In some embodiments, the use of a linker as described herein to join an antibody heavy chain and light chain variable region, provides the benefit of permitting optimal flexibility and length to avoid steric hindrance and allow correct folding of the antigen binding domains. Proper conformation of the first and second peptides is essential for antigen recognition and binding.

As used herein, the terms "variable region" or "variable domain" are used interchangeably and mean a portion of an antibody, generally, a portion of a light or heavy chain, typically the amino-terminal end of the antibody, and comprising about 100-130 amino acids in the heavy chain and about 90 to 115 amino acids in the light chain, which differ extensively in sequence among antibodies and are used in the binding and specificity of a particular antibody for a particular antigen. The variability in sequence is concentrated in those regions called complementarity determining regions (CDRs) while the more highly conserved regions in the variable domain are called framework regions (FR). The CDRs of the light and heavy chains are primarily responsible for the interaction and specificity of the antibody with antigen.

In certain embodiments, the variable region of an antigen binding molecule is a human variable region. In further embodiments, the variable region comprises rodent, human or murine CDRs and human framework regions (FRs). In further embodiments, the variable region is a primate (e.g., a non-human primate) variable region. In yet further embodiments, the variable region is a rabbit variable region. In other embodiments, the variable region comprises human CDRs and non-human (e.g., rabbit, murine, rat or non-human primate) framework regions (FRs). In other embodiments, the variable region comprises non-human (e.g., rabbit, murine, rat or non-human primate) CDRs and human framework regions (FRs).

The terms "VH," "VH domain" and "VH chain" are used interchangeably and mean the heavy chain variable region of an antigen binding molecule, antibody or an antigen binding fragment thereof. As used herein, the term "heavy chain" when used in reference to an antibody may refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

The terms "VL," "VL domain" and "VL chain" are used interchangeably and mean the light chain variable region of an antigen binding molecule, antibody or an antigen binding fragment thereof. As used herein, the term "light chain" when used in reference to an antibody may refer to any distinct type, e.g., kappa (κ) or lambda (λ) based on the amino acid sequence of the constant domains. Light chain amino acid sequences are well known in the art. In specific embodiments, the light chain is a human light chain.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')$_2$, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In further embodiments, the antigen binding molecule is an antibody or fragment thereof, including one or more of the complementarity determining regions (CDRs) thereof. In further embodiments, the antigen binding molecule is a single chain variable fragment (scFv).

As used herein, the terms "single-chain antibody" and "single chain fragment variable (scFv)" are used interchangeably and mean an antigen binding molecule in which a VL and a VH region are joined via a linker to form a continuous protein chain wherein the linker is long enough to allow the protein chain to fold back on itself and form a monovalent antigen binding site (see, e.g., Bird et al., (1988) *Science* 242:423-26 and Huston et al., (1988) *Proc. Natl. Acad. Sci. U.S.A.* 85:5879-83 (1988). FMC63 (Nicholson et al., (1997) *Mol. Immunol.* 34: (16-17) 1157-65) is a specific example of a scFv, and is specific for CD19.

In some embodiments, the antigen binding molecule is a scFv.

In some embodiments, the present invention provides antigen binding molecules, including scFv, that comprise a consensus sequences BPXXXZ, XBPXXXZX or exemplary linker sequence as described herein (e.g., KPGSGE (SEQ ID NO: 4), GKPGSGE (SEQ ID NO: 5), GKPGSGG (SEQ ID NO: 6), GGGSGKPGSGEGGGS (SEQ ID NO: 7), GGGSGKPGSGEGGGGS (SEQ ID NO: 8), GGGGSGKPGSGGGGS (SEQ ID NO: 9), GGGGSGKPGSGEGGS (SEQ ID NO: 10), GGGGSGKPGSGEGGGS (SEQ ID NO: 11), GGGGSGKPGSGEGGGGS (SEQ ID NO: 12), STSGSGKPGSGEGST (SEQ ID NO: 17), GGGGSGGGGSGGGGSG (SEQ ID NO: 18), GGGGSGGGGSGGGGS (SEQ ID NO: 19) or GGGGSGGGGSGGGGS (SEQ ID NO: 20). In some embodiments, the molecules comprising these sequences and cells presenting such molecules, polynucleotides encoding the antigen binding molecules are also provided, and form an aspect of the instant disclosure.

As used herein, the term "binding affinity" means the strength of the sum total of non-covalent interactions between a single binding site of a molecule (e.g., an antigen binding molecule such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y may generally be represented by the dissociation constant (Kd). Affinity may be measured and/or expressed in a number of ways known in the art, including, but not limited to, equilibrium dissociation constant (Kd), and equilibrium association constant (Ka). The Kd is calculated from the quotient of koff/kon, whereas Ka is calculated from the quotient of kon/koff. kon refers to the association rate constant of, e.g., an antibody to an antigen, and koff refers to the dissociation of, e.g., an antibody to an antigen. The kon and koff may be determined by standard techniques known to one of ordinary skill in the art, such as BIAcore® or KinExA or surface plasmon resonance.

In certain embodiments, an antigen binding molecule comprises a single chain, wherein the heavy chain variable region and the light chain variable region are connected by a linker as described herein, to form a scFv (e.g., an antigen binding molecule of instant disclosure). In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 9, at least about 10, at least about 11, at least about 12, at least about 13, at least about 14, at least about 15, at least about 16, at least about 17, at least about 18, at least about 19, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises between about 8 amino acids and about 18 amino acids (e.g., 16 amino acids).

Chimeric Antigen Receptors

An antigen binding molecule may form a component of a CAR or TCR, and may serve to direct the CAR or TCR to recognize a target of interest. As used herein, in the context of a CAR or TCR, an antigen binding molecule means any component of a CAR or TCR that directs the CAR or TCR to a desired target and associates with that target. In specific embodiments, an antigen binding molecule component of a CAR or TCR comprises a scFv comprising a heavy and light chain variable region joined by a linker described herein. The heavy and light variable regions may be derived from the same antibody or two different antibodies. Antigen binding molecules used in a CAR or TCR may be derived from an antibody known or suspect to bind to a target of interest.

T cells may be engineered to express, for example, a chimeric antigen receptor (CAR) or a T cell receptor (TCR). CAR positive (CAR+) T cells are engineered to express a CAR. CARs may comprise, e.g., an extracellular single chain variable fragment (scFv) with specificity for a particular tumor antigen, which is directly or indirectly linked to an intracellular signaling part comprising at least one costimulatory domain, which is directly or indirectly linked to at least one activating domain; the components may be arranged in any order. The costimulatory domain may be derived from, e.g., CD28 or 4-1BB, and the activating domain may be derived from, e.g., any form of CD3-zeta. In certain embodiments, the CAR is designed to have two, three, four, or more costimulatory domains. A CAR scFv may be designed to target, for example, CD19, which is a transmembrane protein expressed by cells in the B cell lineage, including all normal B cells, and B cell malignances such as NHL, CLL, and non-T cell ALL. In some embodiments, a CAR is engineered such that the costimulatory domain is expressed as a separate polypeptide chain. Examples of CAR T cell therapies and constructs are described in U.S. Patent Publication Nos. 2013/0287748, 2014/0227237, 2014/0099309, and 2014/0050708, which are incorporated by reference in their entirety for any purpose.

An antigen binding molecule of the instant disclosure may also be a fully human monoclonal antibody, from which a scFv may be generated, which may then form a component of a CAR or TCR provided herein. Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., (1997) Curr. Opin. Biotechnol. 8:455-58).

It will further be appreciated that where desired, the various domains and regions described herein may be expressed in a separate chain from the antigen binding molecule (e.g., scFv) and activating domains, in so-called "trans" configuration. Thus, in one embodiment an activating domain may be expressed on one chain, while the antigen binding molecule, and/or an extracellular domain, and/or a transmembrane domain and/or a costimulatory domain (depending on the desired construction of the CAR or TCR) may be expressed on a separate chain.

Additionally, the N to C-terminal, or extracellular to intracellular, order of the components of a CAR of the instant disclosure may be varied as desired. The antigen binding molecule (the scFv) will be extracellular in order to be associated with the target antigen, and may include a leader or signal peptide at the N terminal end of the scFv that is most distal to the cell membrane.

Polynucleotides

In one aspect, the present invention provides a polynucleotide encoding a linker as described herein. In some embodiments, the present invention provides a polynucleotide encoding a fusion protein as described herein. The instant disclosure is also directed to polynucleotides encoding antibodies and antigen binding molecules, such as a scFv, that comprising a linker as described herein, molecules comprising this sequence and cells presenting such molecules.

Expression Vectors

In one aspect, the present invention provides an expression vector comprising a polynucleotide encoding a linker or fusion protein as described herein. In certain aspects, provided herein are vectors comprising a polynucleotide of the instant disclosure. In some embodiments, the instant disclosure is directed to a vector or a set of vectors comprising a polynucleotide encoding a linker, or fusion protein, as described herein. In other embodiments, the instant disclosure is directed to a vector or a set of vectors comprising a polynucleotide encoding an antibody or an antigen binding molecule thereof, as disclosed herein.

Any vector known in the art may be suitable for the instant disclosure. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof. In some embodiments of the instant disclosure one, two or more vectors may be employed.

Recombinant Cells

In some embodiments, the present invention provides a recombinant cell comprising a polynucleotide encoding a linker or fusion protein as described herein. In some embodiments, the recombinant cell comprises an expression vector comprising a polynucleotide encoding a linker or fusion protein as described herein. In some aspects, provided herein are cells comprising a polynucleotide or a vector of the instant disclosure. In some embodiments, the instant disclosure is directed to host cells, such as in vitro cells, comprising a polynucleotide encoding a linker or fusion protein, as described herein. In some embodiments, the instant disclosure is directed to host cells, e.g., in vitro cells, comprising a polynucleotide encoding an antibody or an antigen binding molecule thereof, as disclosed herein.

Suitable host cells may be derived from a variety of organisms, including, but not limited to, mammals, plants, birds (e.g., avian systems), insects, yeast, and bacteria. In some embodiments, host cells are mammalian cells. Any mammalian cell susceptible to cell culture, and to expression of polypeptides, may be utilized in accordance with the present invention as a host cell. Non-limiting examples of mammalian cells that may be used in accordance with the present invention include human embryonic kidney 293 cells (HEK293), HeLa cells; BALB/c mouse myeloma line (NSO/l, ECACC No: 85110503); human retinoblasts (PER.C6 (CruCell, Leiden, The Netherlands)); monkey kidney CV1 line transformed by SV40 (COS-7, ATCC CRL 1651); human fibrosarcomacell line (e.g., HT-1080); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; a human hepatoma line (Hep G2), human cell line CAP and AGE1.HN, and Glycotope's panel.

Non-limiting examples of host cells suitable for the present invention include cells and cell lines derived from *Pichia pastoris, Pichia methanolica, Pichia angusta, Schizosacccharomyces pombe, Saccharomyces cerevisiae*, and *Yarrowia lipolytica* for yeast; *Spodoptera frugiperda, Trichoplusis ni, Drosophila melangoster* and *Manduca sexta* for insects; and *Escherichia coli, Salmonella typhimurium, Bacillus subtilis, Bacillus lichenifonnis, Bacteroides fragilis, Clostridia perfringens, Clostridia difficile* for bacteria; and *Xenopus Laevis* from amphibian.

Additionally, any number of available hybridoma cell lines may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

EXAMPLES

While certain compounds, compositions and methods of the present invention have been described with specificity in accordance with certain embodiments, the following examples serve only to illustrate the compounds of the invention and are not intended to limit the same.

Example 1: Epitope Mapping to Identify Linker Consensus Sequence

The specific binding of antibody Clone 8 and 16 raised against a CAR comprising the linker sequence of GST-SGSGKPGSGEGSTKG (SEQ ID NO: 1), were used for epitope mapping ELISA experiments of the full length SEQ ID NO: 1 and variants truncated on either the N- or C-terminus and containing either a biotin moiety on the N-terminus, or a lysine residue with a biotin moiety on the C-terminus (SEQ ID NOs: 21-30).

The antibodies were captured in 96-well plate format using plates pre-coated with Protein G (Pierce). The plates were washed 6× in PBST buffer followed by incubation with target peptides. An additional 6× wash was performed with PBST and the antibodies were further incubated with streptavidin-HRP. Upon a final 6× wash in PBST, signal was detected and quantified via enhanced chemiluminescense kit (ECL, from GE Healthcare) and a Varioskan Flash plate reader (Thermo Fisher). The results of epitope mapping ELISA experiments, shown in FIG. 2 demonstrate that although both antibodies bind to the full length 18mer (SEQ ID NO: 1), Clone 8 specifically binds to the 7mer subsequence GKPGSGE (SEQ ID NO: 5) and Clone 16 specifically binds to the 5mer subsequence KPGSG (SEQ ID NO: 16). Taken together, these data were used to generate a consensus sequence based on the minimal binding epitopes for clone 8 and 16.

Example 2: Antibody Binding Profile of Exemplary Linker Sequences

Figure 3:
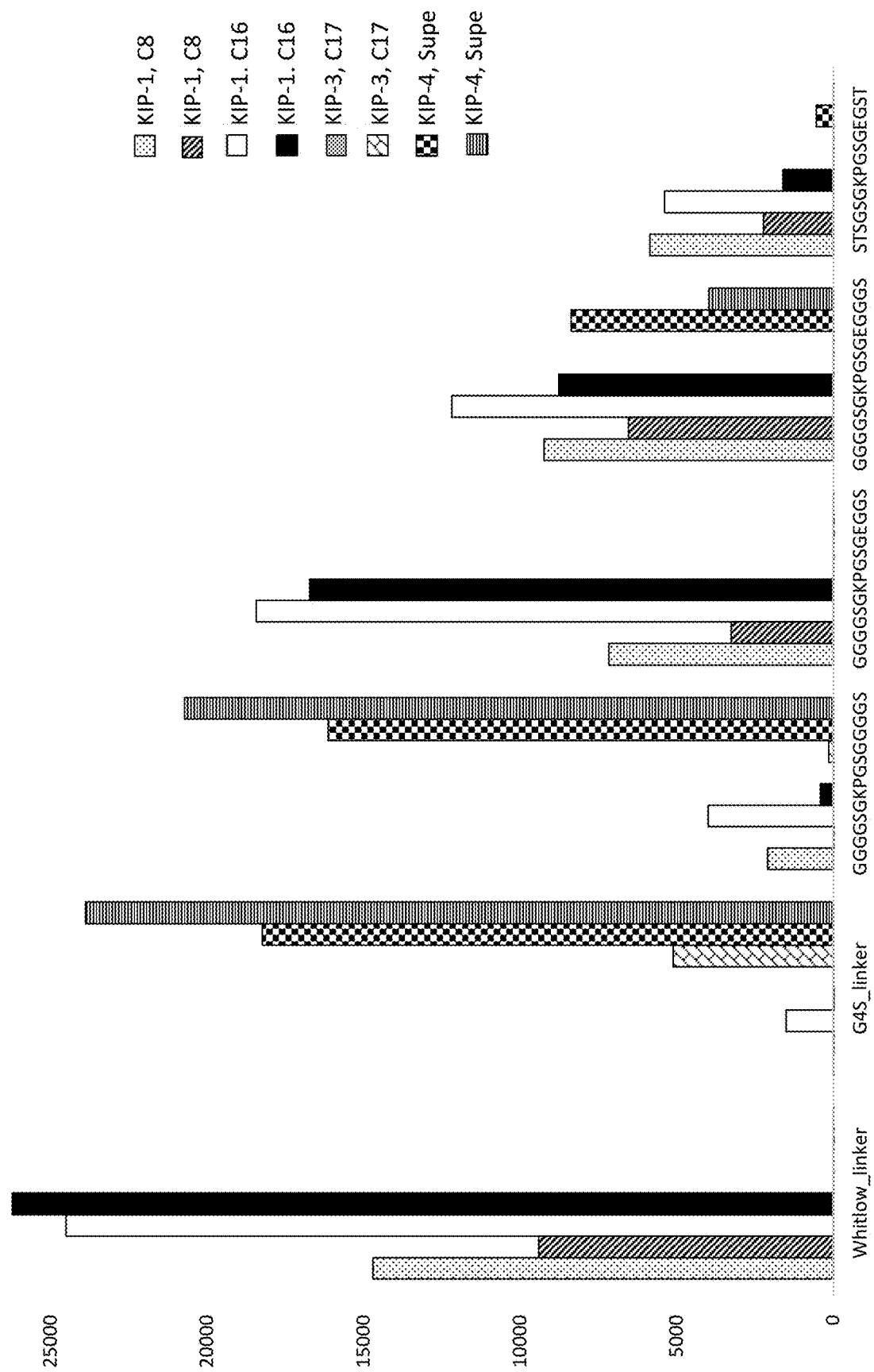
FIG. 3 shows a bar graph of the results of antibody binding profiles of polypeptide linkers comprising SEQ ID Nos 32, 9-11 and 17, respectively.
Figure 4A:
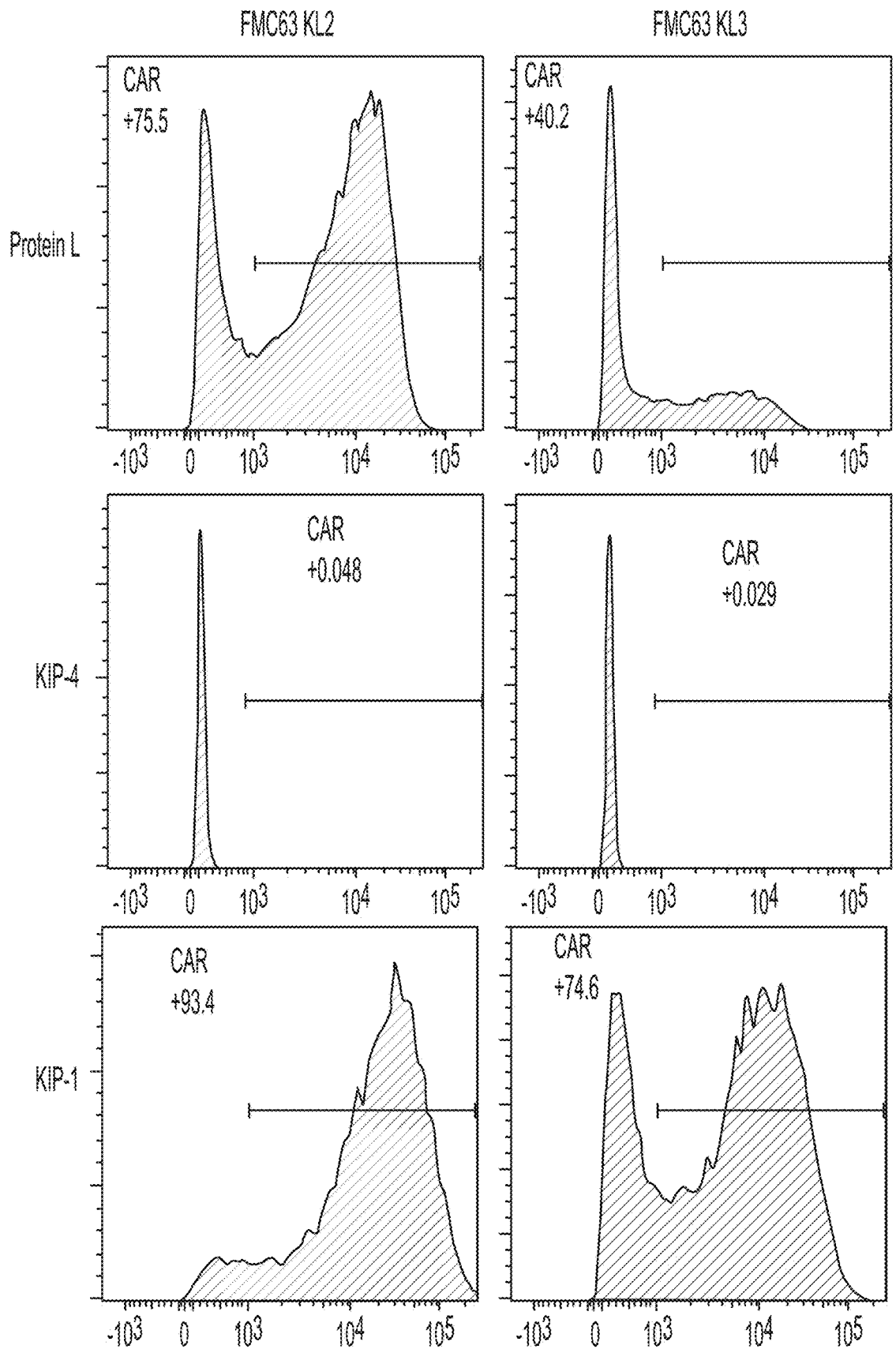
FIGS. 4A-4G are a series of plots showing the results of flow cytometry experiments performed using cells presenting a chimeric antigen receptor (CAR) comprising the peptide KL2 (SEQ ID NO: 10), KL3 (SEQ ID NO: 11), KL4 (SEQ ID NO: 7), KL5 (SEQ ID NO: 12), KL6 (SEQ ID NO: 8), and G4S2 (SEQ ID NO: 18).
Figure 4B:
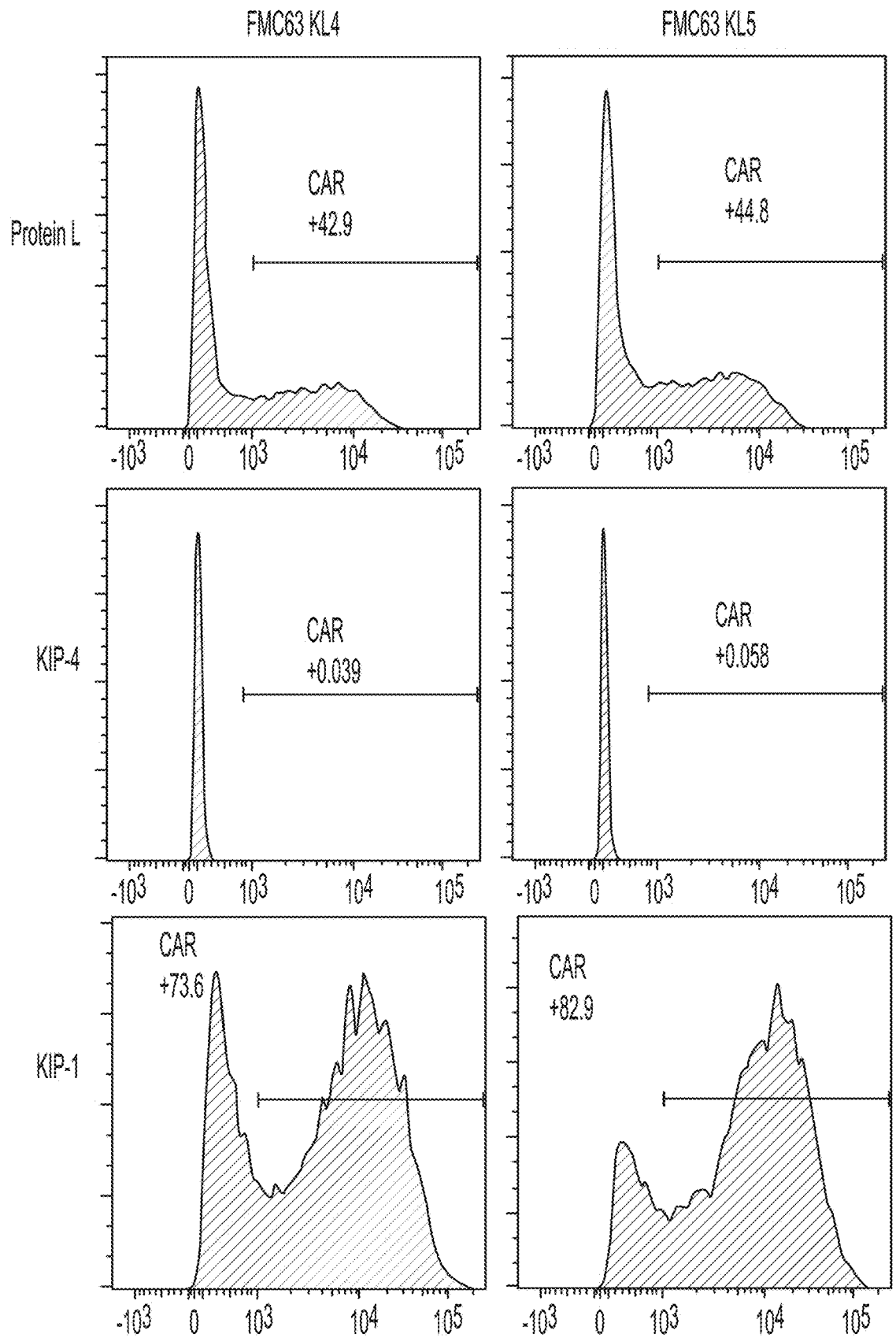
Figure 4C:
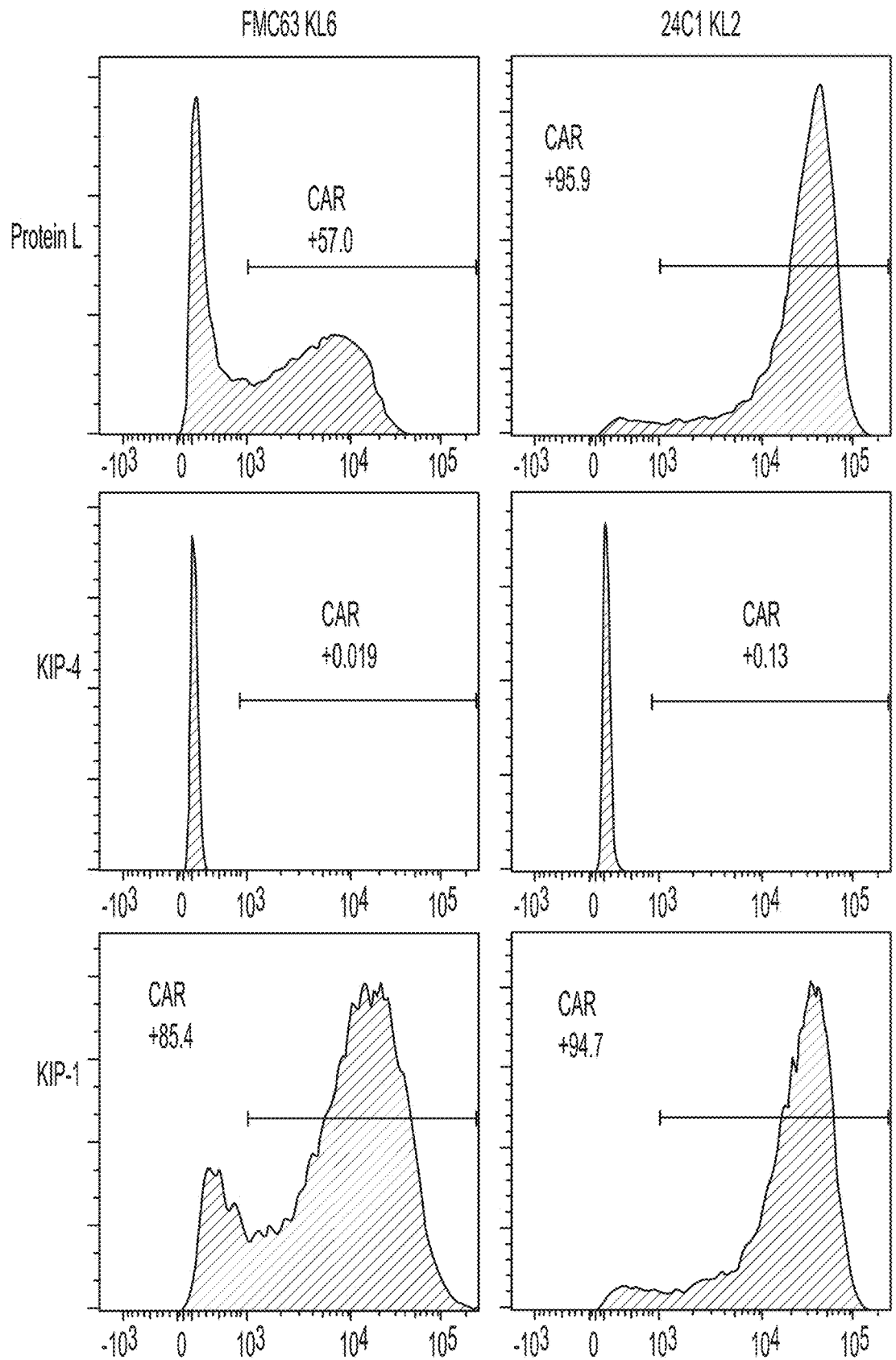
Figure 4D:
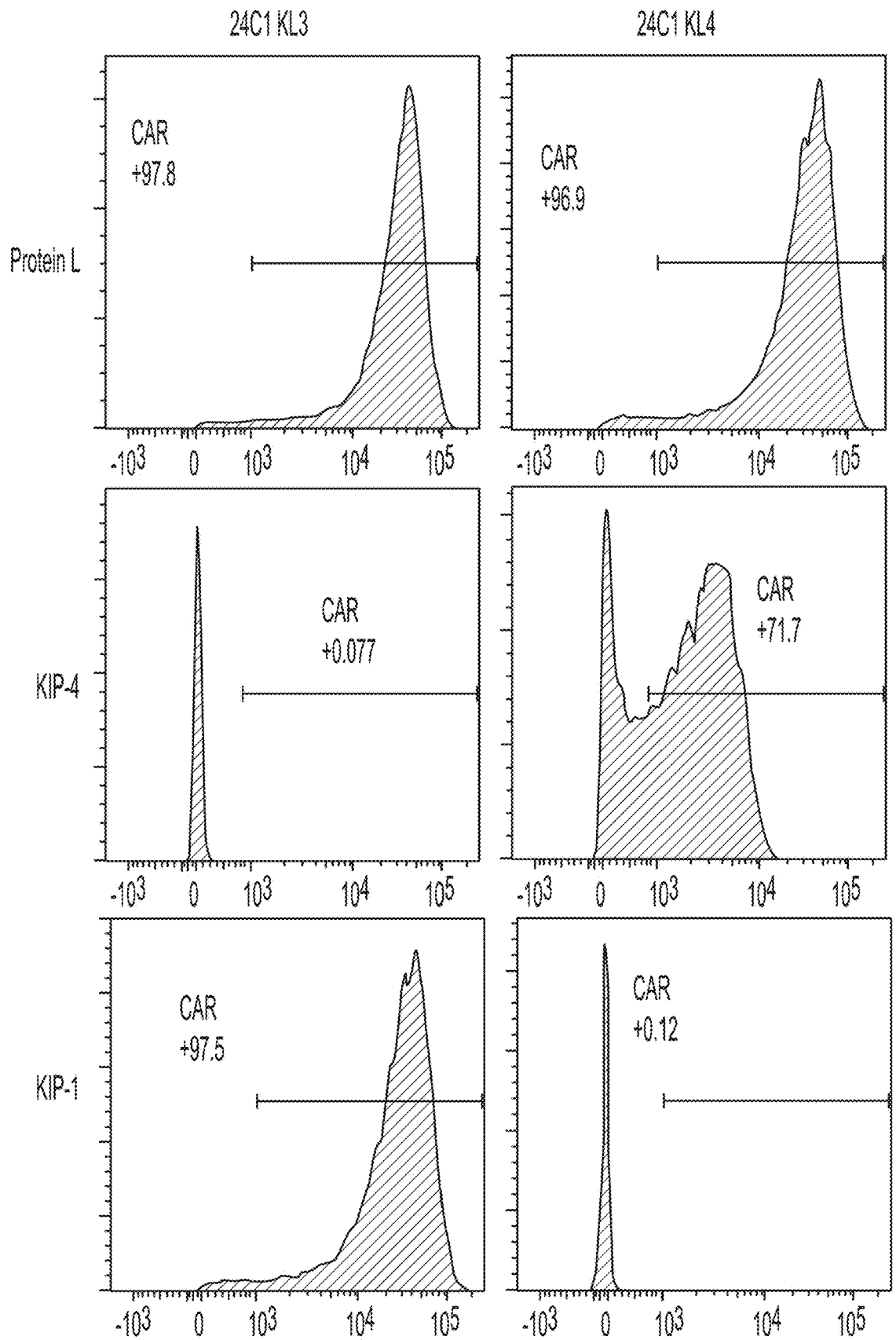
Figure 4E:
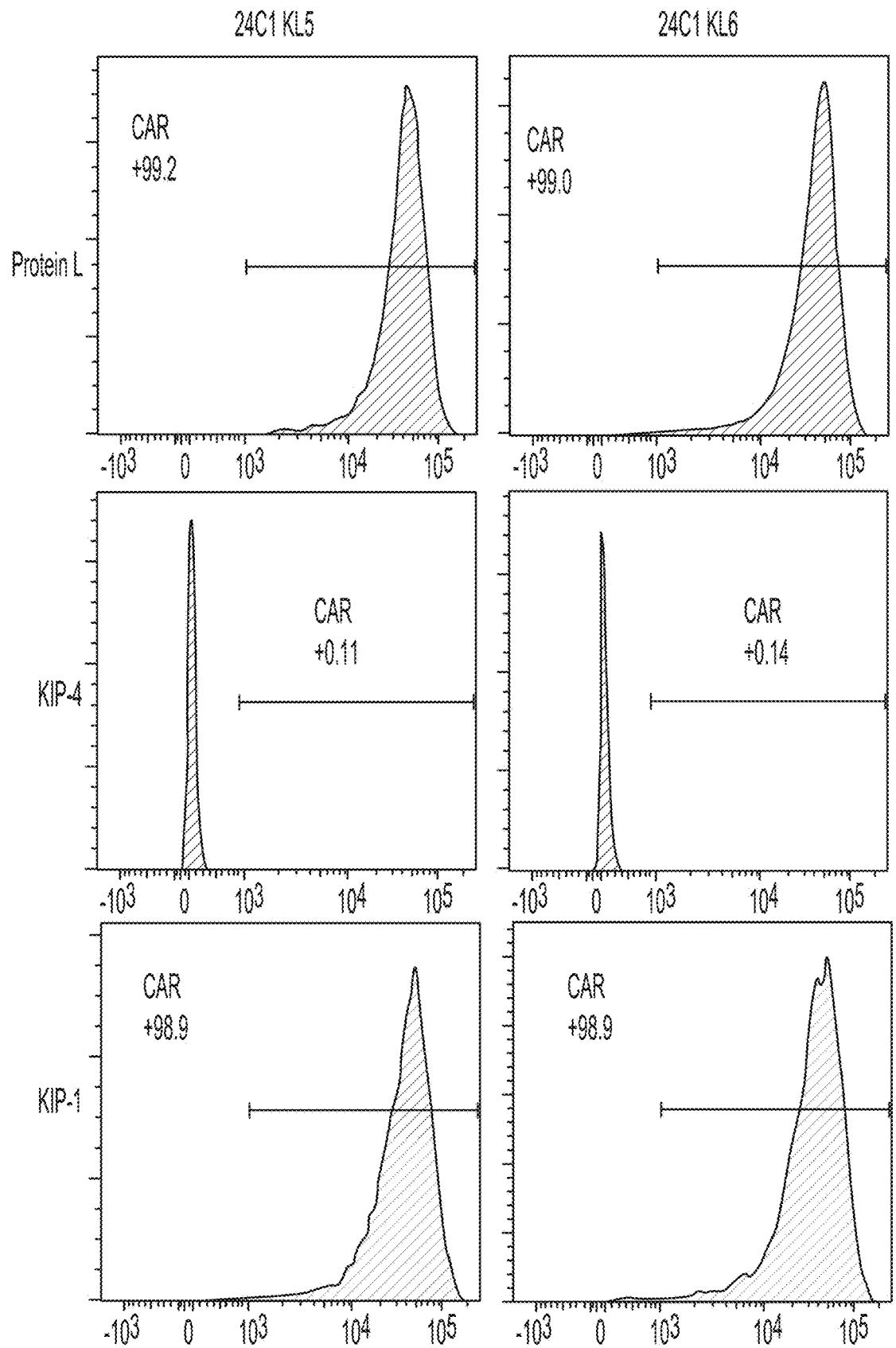
Figure 4F:
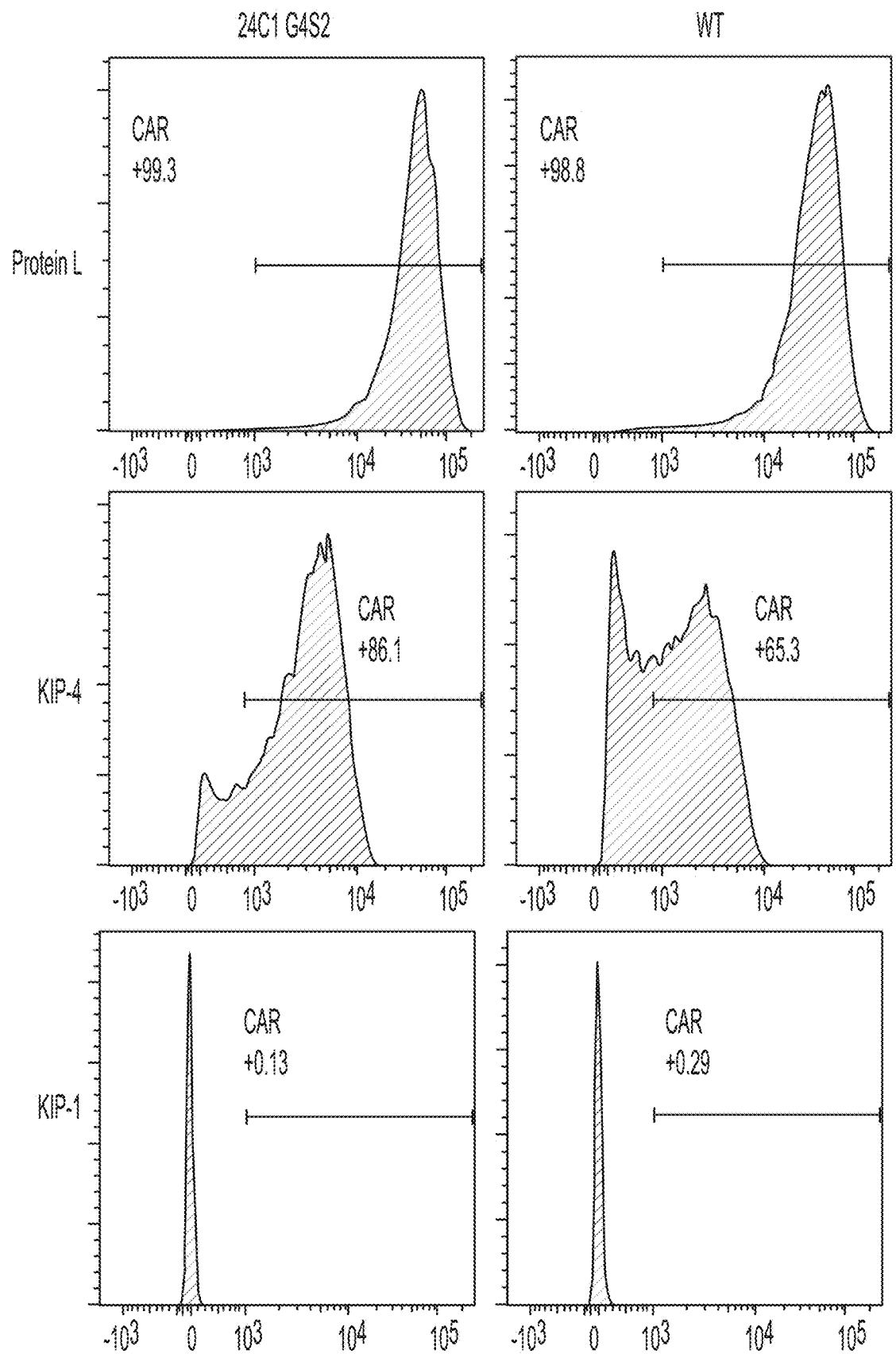
Figure 4G:
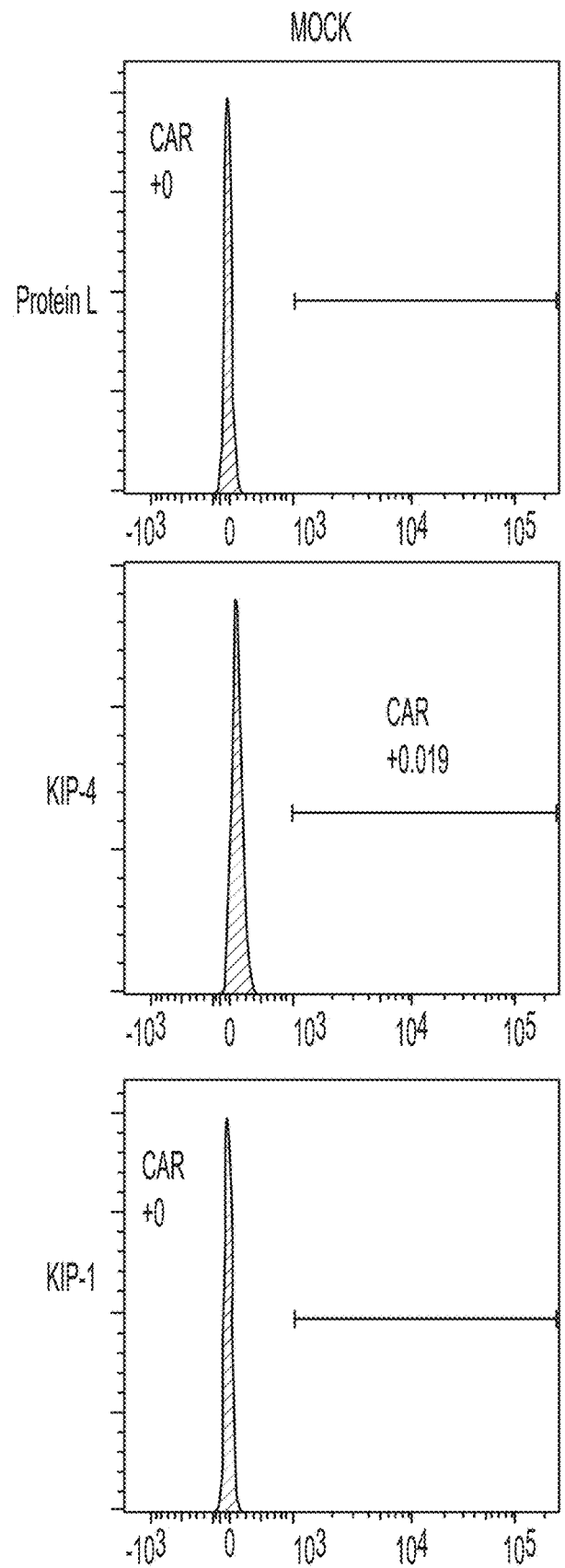

The specific binding of a panel of antibodies raised against a CAR comprising the linker sequence of GST-SGSGKPGSGEGSTKG (SEQ ID NO: 1), the linker sequence GGGGSGGGGSGGGGS (SEQ ID NO: 2), or the or the anti-CD19 scFv clone FMC63 were used to determine the antibody binding profile of exemplary linker sequences from the KIP-1, KIP-4, and KIP-3 antibodies respectively, as described herein. Also included in this assay were peptides comprising linker sequences KL1 (SEQ ID NO: 9), KL2 (SEQ ID NO: 10), KL3 (SEQ ID NO: 11), and the truncated Whitlow linker (SEQ ID NO: 17) described in FIG. 1. The antibodies were captured in 96-well plate format using plates pre-coated with Protein G (Pierce). The plates were washed 6× in PBST buffer followed by incubation with target peptides. An additional 6× wash was performed with PBST and the antibodies were further incubated with streptavidin-HRP. Upon a final 6× wash in PBST, signal was detected and quantified via enhanced chemiluminescense kit (ECL, from GE Healthcare) and a Varioskan Flash plate reader (Thermo Fisher). The results of the antibody profile ELISA experiments, shown in FIG. 3 demonstrate the breadth of antibody binding of linkers according to the present invention.

Example 3: Flow Cytometry Results of CAR Expressing Cells Comprising Chimeric Linkers CAR T cells were assayed via flow cytometry using Protein L as a control to confirm the expression of each CAR construct comprising the linker sequences SEQ ID NO: 1 (FMC63 WT), or the SEQ ID NO: 2 (FMC63 G4S). These results confirm expression of the CAR constructs on the surface of T cells. As shown in FIGS. 4A-4G, CAR T cells were produced in the context of scFv FMC63 and 24C1 scFv. KL2 (SEQ ID NO: 10), KL3 (SEQ ID NO: 11), KL4 (SEQ ID NO: 7), KL5 (SEQ ID NO: 12), KL6 (SEQ ID NO: 8), and G4S2 (SEQ ID NO: 18) linkers were used to link the VL and VH domains of the scFv.

Sequences and SEQ ID NOs

The instant disclosure comprises a number of nucleic acid and polypeptide sequences. For convenience, Table B below correlates each sequence with its appropriate SEQ ID NO.

TABLE B

| SEQ ID NO | Sequence |
|---|---|
| SEQ ID NO: 1 | GSTSGSGKPGSGEGSTKG |
| SEQ ID NO: 2 | GGGGSGGGSGGGGS |
| SEQ ID NO: 3 | xxxGKPGSGExxxGKPGSGExxx |
| SEQ ID NO: 4 | KPGSGE |
| SEQ ID NO: 5 | GKPGSGE |
| SEQ ID NO: 6 | GKPGSGG |
| SEQ ID NO: 7 | GGGSGKPGSGEGGGS |
| SEQ ID NO: 8 | GGGSGKPGSGEGGGGS |
| SEQ ID NO: 9 | GGGGSGKPGSGGGGS |
| SEQ ID NO: 10 | GGGGSGKPGSGEGGS |
| SEQ ID NO: 11 | GGGGSGKPGSGEGGGS |
| SEQ ID NO: 12 | GGGGSGKPGSGEGGGGS |
| SEQ ID NO: 13 | GSGKPGSGEG |
| SEQ ID NO: 14 | GKPGSGEG |
| SEQ ID NO: 15 | SGKPGSGE |
| SEQ ID NO: 16 | KPGSG |
| SEQ ID NO: 17 | STSGSGKPGSGEGST |
| SEQ ID NO: 18 | GGGGSGGGSGGGGSG |
| SEQ ID NO: 19 | GGGGSGGGSGGGGS |
| SEQ ID NO: 20 | GGGGSGGGSGGGGS |
| SEQ ID NO: 21 | GSTSGSGKPGSGEGST |
| SEQ ID NO: 22 | GSTSGSGKPGSGEG |
| SEQ ID NO: 23 | GSTSGSGKPGSGE |
| SEQ ID NO: 24 | GSTSGSGKPGSG |
| SEQ ID NO: 25 | GSTSGSGKPG |
| SEQ ID NO: 26 | GSGKPGSGEGSTKG |
| SEQ ID NO: 27 | SGKPGSGEGSTKG |
| SEQ ID NO: 28 | GKPGSGEGSTKG |
| SEQ ID NO: 29 | KPGSGEGSTKG |

TABLE B-continued

| SEQ ID NO | Sequence |
|---|---|
| SEQ ID NO: 30 | PGSGEGSTKG |
| SEQ ID NO: 31 | GSGKPGSGEGG |
| SEQ ID NO: 32 | GGGGS |

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) may be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention may be explicitly excluded from the claims, regardless of whether the specific exclusion is recited in the specification. The publications, websites and other reference materials referenced herein to describe the background of the invention and to provide additional detail regarding its practice are hereby incorporated by reference.

The invention claimed is:

1. A fusion protein comprising:
a first polypeptide and a second polypeptide covalently linked by a peptide comprising a consensus sequence GKPGSGZ (SEQ ID NO: 33), wherein the peptide is 7-17 amino acids in length;
wherein the peptide is not GSTSGSGKPGSGEGSTKG (SEQ ID NO: 1), GSGKPGSGEG (SEQ ID NO: 13), GKPGSGEG (SEQ ID NO: 14), or SGKPGSGE (SEQ ID NO: 15),
wherein the peptide is selected from the group consisting of GKPGSGG (SEQ ID NO: 6), GSGKPGSGEGG (SEQ ID NO: 31), GGGSGKPGSGEGGGS (SEQ ID NO: 7), GGGSGKPGSGEGGGGS (SEQ ID NO: 8), GGGGSGKPGSGGGGS (SEQ ID NO: 9), GGGGSGKPGSGEGGS (SEQ ID NO: 10), GGGGSGKPGSGEGGGS (SEQ ID NO: 11), GGGGSGKPGSGEGGGGS (SEQ ID NO: 12), and STSGSGKPGSGEGST (SEQ ID NO: 17),
wherein the fusion protein is a CD19 specific scFv fusion protein comprising a light chain variable domain and a heavy chain variable domain, and
wherein the first polypeptide comprises the light chain variable region and the second polypeptide comprises the heavy chain variable domain.

2. A polynucleotide encoding any one of the peptide according to claim 1.

3. A polynucleotide encoding the fusion protein of claim 1.

4. An expression vector comprising the polynucleotide of claim 3.

5. A recombinant cell comprising the polynucleotide of claim 3.

6. The recombinant cell of claim 5, wherein the cell is an immune cell.

7. The immune cell of claim 6, wherein the immune cell is a T cell, NK cell, or a stem cell.

* * * * *